US010023560B2

(12) United States Patent
Boss et al.

(10) Patent No.: US 10,023,560 B2
(45) Date of Patent: Jul. 17, 2018

(54) CRYSTALLINE SALT FORM OF (S)-(2-(6 CHLORO-7-METHYL-1H-BENZO[D] IMIDAZOL-2-YL)-2-METHYLPYRROLIDIN-1-YL)(5-METHOXY-2-(2H-1,2,3-TRIAZOL-2-YL)PHENYL)METHANONE AS OREXIN RECEPTOR ANTAGONIST

(71) Applicant: IDORSIA PHARMACEUTICALS LTD, Allschwil (CH)

(72) Inventors: Christoph Boss, Allschwil (CH); Christine Brotschi, Allschwil (CH); Markus Gude, Allschwil (CH); Bibia Heidmann, Allschwil (CH); Thierry Sifferlen, Allschwil (CH); Markus Von Raumer, Allschwil (CH); Jodi T. Williams, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/702,281

(22) Filed: Sep. 12, 2017

(65) Prior Publication Data
US 2018/0002317 A1    Jan. 4, 2018

Related U.S. Application Data

(62) Division of application No. 15/101,832, filed as application No. PCT/IB2014/066509 on Dec. 2, 2014, now Pat. No. 9,790,208.

(30) Foreign Application Priority Data

Dec. 3, 2013  (WO) ............... PCT/IB2013/060595

(51) Int. Cl.
C07D 403/14    (2006.01)

(52) U.S. Cl.
CPC ........ *C07D 403/14* (2013.01); *C07B 2200/13* (2013.01)

(58) Field of Classification Search
CPC .................... C07D 403/14; A61K 31/4184
See application file for complete search history.

(56) References Cited

U.S. PATENT DOCUMENTS

| 3,282,927 | A |   | 11/1966 | Montzka et al. |
| 9,790,208 | B2 | * | 10/2017 | Boss ................... C07D 403/14 |
| 2015/0252032 | A1 |   | 9/2015 | Boss et al. |

FOREIGN PATENT DOCUMENTS

| JP | 2005501027 | 1/2005 |
| WO | WO 2001/096302 | 12/2001 |
| WO | WO 2002/028839 | 4/2002 |
| WO | WO 2002/044172 | 6/2002 |
| WO | WO 2002/089800 | 11/2002 |
| WO | WO 2002/090355 | 11/2002 |
| WO | WO 2003/002559 | 1/2003 |
| WO | WO 2003/002561 | 1/2003 |
| WO | WO 2003/032991 | 4/2003 |
| WO | WO 2003/041711 | 5/2003 |
| WO | WO 2003/051368 | 6/2003 |
| WO | WO 2003/051873 | 6/2003 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2005/118548 | 12/2005 |
| WO | WO 2007/105177 | 9/2007 |
| WO | WO 2008/020405 | 2/2008 |
| WO | WO 2008/038251 | 4/2008 |
| WO | WO 2008/069997 | 6/2008 |
| WO | WO 2008/081399 | 7/2008 |
| WO | WO 2008/087611 | 7/2008 |
| WO | WO 2008/117241 | 10/2008 |
| WO | WO 2008/139416 | 11/2008 |
| WO | WO 2008/150364 | 12/2008 |
| WO | WO 2009/003993 | 1/2009 |
| WO | WO 2009/003997 | 1/2009 |
| WO | WO 2009/004584 | 1/2009 |
| WO | WO 2009/016560 | 2/2009 |
| WO | WO 2009/016564 | 2/2009 |
| WO | WO 2009/040730 | 4/2009 |
| WO | WO 2009/047723 | 4/2009 |
| WO | WO 2009/104155 | 8/2009 |
| WO | WO 2009/124956 | 10/2009 |
| WO | WO 2010/004507 | 1/2010 |
| WO | WO 2010/038200 | 4/2010 |
| WO | WO 2010/060470 | 6/2010 |
| WO | WO 2010/060471 | 6/2010 |
| WO | WO 2010/060472 | 6/2010 |
| WO | WO 2010/063662 | 6/2010 |
| WO | WO 2010/063663 | 6/2010 |
| WO | WO 2010/072722 | 7/2010 |
| WO | WO 2010/122151 | 10/2010 |
| WO | WO 2012/025877 | 3/2012 |

(Continued)

OTHER PUBLICATIONS

Brittain, Harry G, "X-ray Diffraction III: Pharmaceutical Applications of X-ray Powder Diffraction", Spectroscopy, vol. 16(7), p. 14-18, (2001).
U.S. Pharmacopia-National Formulary, General Chapter 18: X-ray Diffraction, USP 23/NF, p. 1843-1844, (1995).
U.S. Appl. No. 15/644,547, filed Jul. 7, 2017, Boss et al.
Adam et al., "Stress, Eating and the Reward System", Physiology & Behavior, vol. 91, No. 4, p. 449-458, (2007).
Aston-Jones et al., "Lateral hypothalamic orexin/hypocretin neurons: A role in 3 reward-seeking and addiction", Brain Research, vol. 1314, p. 74-90, (2009).
Attia et al., "Anorexia Nervosa", Merck Manual Home Edition, accessed on Nov. 30, 2011 at www.merckmanuals.com/home/print/mental_health_disorders/eating_disorders/anorexia_nervosa.html.

(Continued)

*Primary Examiner* — Golam M Shameem
(74) *Attorney, Agent, or Firm* — Hoxie & Associates LLC

(57) ABSTRACT

The invention relates to a crystalline form of (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl) methanone hydrochloride, processes for the preparation thereof, pharmaceutical compositions containing said crystalline form, and its use as medicament, especially as orexin receptor antagonist.

13 Claims, 2 Drawing Sheets

(56) References Cited

FOREIGN PATENT DOCUMENTS

| | | |
|---|---|---|
| WO | WO 2012/063207 | 5/2012 |
| WO | WO 2012/110986 | 8/2012 |
| WO | WO 2013/068935 | 5/2013 |
| WO | WO 2013/158776 | 10/2013 |
| WO | WO 2013/182972 | 12/2013 |
| WO | WO 2014/141065 | 9/2014 |
| WO | WO 2015/083070 | 6/2015 |
| WO | WO 2015/083094 | 6/2015 |

OTHER PUBLICATIONS

Becker et al., "Why do so many drugs for Alzheimer's disease fail in development? Time for New Methods and New Practices?" J. Alzheimer's Disease, vol. 15, No. 2, p. 303-325, (2008).
Berridge et al., "Hypocretin/orexin in arousal and stress", Brain Research, vol. 1314, p. 91-102, (2009).
Borgland et al., "Orexin A in the VTA is Critical for the Induction of Synaptic Plasticity and Behavioral Sensitization to Cocaine", Neuron, vol. 49, No. 4, p. 589-601, (2006).
Boss et al., "Biomedical Application of Orexin/Hypocretin Receptor Ligands in Neuroscience", Journal of Medicinal Chemistry, vol. 52, p. 891-903, (2009).
Boutrel et al., "Role for hypocretin in mediating stress-induced reinstatement of cocaine-seeking behavior", Proc Natl Acad. Sci., vol. 102, No. 52, p. 19168-19173, (2005).
Brittain et al., "Polymorphism in Pharmaceutical Dosage Forms—Methods for the Characterization of Polymorphs", Polymorphism in Pharmaceutical Solids, p. 235-238, (1999).
Brisbare et al., "Promotion of sleep by targeting the orexin system in rats, dogs and humans", Nature Medicine, vol. 13, p. 150-155, (2007).
Carter et al., "The brain hypocretins and their receptors: mediators of allostatic Arousal", Current Opinion in Pharmacology, vol. 9, p. 39-45, (2009).
Chemelli et al., "Narcolepsy in orexin Knockout Mice: Molecular Genetics of Sleep Regulation", Cell Press, vol. 98, p. 437-451, (1999).
Chrousos et al., The Concepts of Stress and Stress System Disorders, JAMA, vol. 267, No. 9, p. 1244-1252, (1992).
Dietrich et al., "Intact learning and memory in rats following treatment with the dual orexin receptor antagonist almorexant", Psychopharmacology vol. 212, p. 145-154, (2010).
European Pharmacopoeia, "5.11. Characters Section in Monographs", p. 637, (2008).
Fendt et al., "The Neuroanatomical and Neurochemical Basis of Conditioned Fear", Neuroscience and Biobehavioral Reviews, vol. 23, p. 743-760, (1999).
Feng et al., "Changes in brain orexin levels in a rat model of depression induced by neonatal administration of clomipramine", J Psychopharmacol, vol. 22, No. 7, p. 784-791, (2008).
Furlong et al., "Hypocretin/orexin contributes to the expression of some but not all forms of stress and arousal", European Journal of Neuroscience, vol. 30, No. 8, p. 1603-1614, (2009).
Gasparini et al., "Peripheral markers in testing pathophysiological hypotheses and diagnosing Alzheimer's disease", FASEB Journal, vol. 12(1), p. 17-34, (2017).
Greicius et al., "Presenile dementia syndromes: an update on taxonomy and diagnosis", J Neurol. Neurosurg. Psychiatry, vol. 72, p. 691-700, (2002).
Gould et al., "Salt Selection for Basic Drugs", International Journal of Pharmaceutics, vol. 33, p. 201-217, (1986).
Gozzi et al., "Functional Magnetic Resonance Imaging Reveals Different Neural Substrates for the Effects of Orexin-1 and Orexin-2 Receptor Antagonists", PLoS One, vol. 6, No. 1, p. E16406, (2011).
Griesser et al., "The Importance of Solvates", Terminology and Classification of Solvates, Chp. 8, p. 211-222, (2006).
Griesser et al., "Polymorphism in the Pharmaceutical Industry: The Importance of Solvates", Chapter 8, p. 200-233, (2006).

Hamamoto et al., "Chemoenzymatic Synthesis of the C-13 side chain of paclitaxel (Taxol) and docetaxel (Taxotere)", Tetrahedron: A symmetry, vol. 11, p. 4485-4497, (2000).
Hollander et al., "Insular hypocretin transmission regulates nicotine reward", Proceedings of the National Academy of Sciences, vol. 105, No. 49, p. 19480-19485, (2008).
Hutcheson et al., "Orexin-1 receptor antagonist SB-334867 reduces the acquisition and expression of cocaine-conditioned reinforcement and the expression of amphetamine-conditioned reward", Behavioral Pharmacology, vol. 22, No. 2, p. 173-181, (2011).
Insel et al., "Rethinking Schizophrenia", Nature, vol. 468 p. 187-193, (2010).
International Search Report of International Application No. PCT/IB2014/066508 dated Feb. 16, 2015, 3 pages.
International Search Report of International Application No. PCT/IB2014/066509 dated Feb. 16, 2015, 3 pages.
Kang et al., "Amyloid-beta dynamics are regulated by orexin and the sleep-wake cycle", Science, vol. 326, No. 5955, p. 1005-1007, (2009).
Kayaba et al., "Attenuated defense response and low basal blood pressure in orexin knockout mice", American Journal of Physiology- Regulatory Integrative Comparative Physiology, vol. 285, p. R581-593, (2003).
Koob et al., "Neurobiological mechanisms of addiction: Focus on corticotropin-releasing factor", Current Opinion Investigational Drugs, vol. 11, No. 1, p. 63-71, (2010).
Langmead et al., "Characterisation of the binding of [3H]-SB-674042, a novel nonpeptide antagonist, to the human orexin-1 receptor", British Journal of Pharmacology, vol. 141, p. 340-346, (2004).
Lawrence et al., "The orexin system regulates alcohol-seeking in rats", British Journal of Pharmacology, vol. 148, No. 6, p. 752-759, (2006).
Lesage et al., "Nicotine self-administration in the rat: effects of hypocretin antagonists and changes in hypocretin mRNA", Psychopharmacology, vol. 209, No. 2, p. 203-212, (2010).
Liu et al., "Insomnia and Hypersomnia Associated with Depressive Phenomenology and Comorbidity in Childhood Depression", Sleep and Childhood Depression, vol. 30, No. 1, p. 83-90, (2007).
Majzoub et al., "Corticotropin-releasing hormone physiology", European Journal of Endocrinology, vol. 155, No. 1, p. S71-S76, (2006).
Mathes et al., "The biology of binge eating", Appetite, vol. 52, p. 545-553, (2009).
Nollet et al., "Activation of orexin neurons in dorsomedial/perifornical hypothalamus and antidepressant reversal in a rodent model of depression", Neuro Pharmacology, vol. 61, No. 1-2, p. 336-46, (2011).
Pouton et al., "Formulation of Lipid-Based Delivery Systems for Oral Administration: Materials, Methods and Strategies", Advanced Drug Delivery Reviews, vol. 60, p. 625-637, (2008).
Prud'Homme et al., Nutritional Status Modulates Behavioural and Olfactory Bulb for Response to Isoamyl Acetate or Food Odour in Rats: Roles of Orexins and Leptin, Neuroscience, vol. 162, No. 4, p. 1287-1298, (2009).
Quarta et al., "The orexin-1 receptor antagonist SB-334867 reduces amphetamine-evoked dopamine outflow in the shell of the nucleus accumbens and decreases the expression of amphetamine sensitization", Neurochem Int., vol. 56, No. 1, p. 11-15, (2009).
Remington, The Science and Practice of Pharmacy, 21st Edition, Part 5, Pharmaceutical Manufacturing; 2005.
Sakurai et al., "Orexins and Orexin Receptors: A family of Hypothalamic Neuropeptides and G Protein-Coupled Receptors that Regulate Feeding Behavior", Cell Press, vol. 92, p. 573-585, (1998).
Salomon et al., "Diurnal Variation of Cerebrospinal Fluid Hypocretin-1 (Orexin-A) Levels in Control and Depressed Subjects", Society of Biological Psychiatry, vol. 54, No. 2, p. 96-104, (2003).
Sharf et al., "Role of orexin/hypocretin in dependence and addiction", Brain Research, vol. 1314, p. 130-138, (2010).
Shippenberg et al., "Recent advances in animal models of drug addiction", Neuropsychopharmacology: The fifth generation of progress, Chp. 97, p. 1381-1397.

(56) References Cited

OTHER PUBLICATIONS

Smith et al., "Orexin/hypocretin is necessary for context-driven cocaine-seeking", Neuropharmacology, vol. 58, No. 1, p. 179-184, (2010).
Smith et al., "Orexin/hypocretin signaling at the orexin 1 receptor regulates cue-elicited cocaine-seeking.", European Journal Neuroscience, vol. 30, No. 3, p. 493-503, (2009).
Spealman et al., "Pharmacological and Environmental Determinants of Relapse to Cocaine-Seeking Behavior", Pharmacology Biochemistry and Behavior, vol. 64, p. 327-336, (1999).
Stahl et al., "Handbook of Pharmaceutical Salts: Properties, Selection, and Use", International Union of Pure and Applied Chemistry, p. 329-350, (2008).
Stickgold et al., "Sleep-dependent memory consolidation", Nature, vol. 437, p. 1272-1278, (2005).
Sutcliffe et al., "The Hypocretins: Setting the arousal threshold", Nature Reviews Neuroscience, vol. 3, No. 5, p. 339-349, (2002).
Tsujino et al., "Orexin/Hypocretin: A Neuropeptide at the Interface of Sleep, Energy Homeostasis, and Reward System", Pharmacological Reviews, vol. 61(2), p. 162-176, (2009).
Vanderschuren et al., "Sensitization Processes in Drug Addiction", Current Topics in behavioral Neurosciences, p. 179-195, (2009).
Vinkers et al., "Translational aspects of pharmacological research into anxiety disorders: The stress-induced hyperthermia (SIH) paradigm", European Journal of Pharmacology, vol. 585, p. 407-425, (2008).
Winrow et al., "Orexin receptor antagonism prevents transcriptional and behavioral plasticity resulting from stimulant exposure", Neuropharmacology, vol. 58, No. 1, p. 185-94, (2009).
Wouters et al., "Pharmaceutical Salts and Co-Crystals", RSC Drug Discovery Series, p. vii-xiv, (2012).
Zhang et al., "Multiple components of the defense response depend on orexin: evidence from orexin knockout mice and orexin neuron-ablated mice", Auton. Neurosci, vol. 126-127, p. 139-145, (2006).

\* cited by examiner

CRYSTALLINE SALT FORM OF (S)-(2-(6 CHLORO-7-METHYL-1H-BENZO[D]IMIDAZOL-2-YL)-2-METHYLPYRROLIDIN-1-YL)(5-METHOXY-2-(2H-1,2,3-TRIAZOL-2-YL)PHENYL)METHANONE AS OREXIN RECEPTOR ANTAGONIST

CROSS REFERENCE TO RELATED APPLICATIONS

This application is a divisional application of U.S. application Ser. No. 15/101,832, filed on Jun. 3, 2016, which claims the benefit of United States Application under 35 U.S.C. 371 of PCT Application No. PCT/IB2014/066509, filed on Dec. 2, 2014, which claims the benefit of and priority to PCT Application No. PCT/IB2013/060595, filed on Dec. 3, 2013, the contents of each of which are incorporated herein by reference.

The invention relates to a novel crystalline salt form of (S)-(2-(6-chloro-7-methyl-1H-benzo[d]imidazol-2-yl)-2-methylpyrrolidin-1-yl)(5-methoxy-2-(2H-1,2,3-triazol-2yl)phenyl)methanone (hereinafter also referred to as "COMPOUND"), processes for the preparation thereof, pharmaceutical compositions containing said crystalline form, and their use as orexin receptor antagonists in the treatment or prevention of sleep disorders, anxiety disorders, addiction disorders, cognitive dysfunctions, mood disorders, or appetite disorders.

Orexins (orexin A or OX-A and orexin B or OX-B) are neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexin receptor antagonists are a novel type of nervous system or psychotropic drugs. Their mode of action in animals and humans involves either blockade of both orexin-1 and orexin-2 receptor (dual antagonists), or individual and selective blockade of either the orexin-1 or the orexin-2 receptor (selective antagonists) in the brain. Orexins were initially found to stimulate food consumption in rats suggesting a physiological role for these peptides as mediators in the central feedback mechanism that regulates feeding behaviour (Sakurai T. et al., Cell, 1998, 92, 573-585).

On the other hand, orexin neuropeptides and orexin receptors play an essential and central role in regulating circadian vigilance states. In the brain, orexin neurons collect sensory input about internal and external states and send short intrahypothalamic axonal projections as well as long projections to many other brain regions. The particular distribution of orexin fibers and receptors in basal forebrain, limbic structures and brainstem regions—areas related to the regulation of waking, sleep and emotional reactivity—suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter ME et al., "The brain hypocretins and their receptors: mediators of allostatic arousal.", Curr Op Pharmacol. 2009, 9: 39-45] that are described in the following sections. It was also observed that orexins regulate states of sleep and wakefulness opening potentially novel therapeutic approaches to insomnia and other sleep disorders (Chemelli R. M. et al., Cell, 1999, 98, 437-451).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declariative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

In addition, both anatomical and functional evidence from in vitro and in vivo studies suggest an important positive interaction of the endogenous orexin system with reward pathways of the brain [Aston-Jones G et al., Brain Res 2010, 1314, 74-90; Sharf R et al., Brain Res 2010, 1314, 130-138]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. Orexin-1 receptor antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397].

Several converging lines of evidence furthermore demonstrate a direct role of the orexin system as modulator of the acute stress response. For instance, stress (i.e. psychological stress or physical stress) is associated with increased arousal and vigilance which in turn is controlled by orexins [Sutcliffe, J G et al., Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., JAMA 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

As outlined above the orexin system regulates homeostatic functions such as sleep-wake cycle, energy balance, emotions and reward. Orexins are also involved in mediating the acute behavioral and autonomous nervous system response to stress [Zhang W et al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., NeuroPharm 2011, 61(1-2):336-46].

The orexin system is also involved in stress-related appetitive/reward seeking behaviour (Berridge C W et al., Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Orexins have been found to increase food intake and appetite [Tsujino, N, Sakurai, T, Pharmacol Rev 2009, 61(2) 162-176]. As an additional environmental factor, stress can contribute to binge eating behaviour, and lead to obesity [Adam, T C et al. Physiol Behav 2007, 91(4) 449-458]. Animal models that are clinically relevant models of binge eating in humans are described for example in W. Foulds Mathes et al.; Appetite 2009, 52, 545-553.

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L., Curr Op Pharmacol. 2009, 9: 39-45; C Boss, C Brisbare-Roch, F Jenck, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155]. The compound further attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/047723) which relates to emotional states of fear and anxiety diseases such as anxieties including phobias and post traumatic stress disorders (PTSDs). In addition, intact declarative and non-declarative learning and memory has been demonstrated in rats treated with this compound [WO2007/105177, H Dietrich, F Jenck, Psychopharmacology 2010, 212, 145-154]. Said compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound has also been shown to induce antidepressant-like activity in a mouse model of depression, when administered chronically [Nollet et al., NeuroPharm 2011, 61(1-2):336-46]. Moreover, the compound has been shown to attenuate the natural activation induced by orexin A in fasted hungry rats exposed to food odors [M J Prud'homme et al., Neuroscience 2009, 162(4), 1287-1298]. The compound also displayed pharmacological activity in a rat model of nicotine self-administration [LeSage M G et al., Psychopharmacology 2010, 209(2), 203-212]. Another dual orexin receptor antagonist, N-biphenyl-2-yl-1-{[(1-methyl-1H-benzimidazol-2-yl)sulfanyl]acetyl}-L-prolinamide inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

Orexin receptor antagonists comprising a 2-substituted saturated cyclic amide derivatives (such as 2-substituted pyrrolidine-1-carboxamides) are known for example from WO2008/020405, WO2008/038251, WO2008/081399, WO2008/087611, WO2008/117241, WO2008/139416, WO2009/004584, WO2009/016560, WO2009/016564, WO2009/040730, WO2009/104155, WO2010/004507, WO2010/038200, WO2001/096302, WO2002/044172, WO2002/089800, WO2002/090355, WO2003/002559, WO2003/032991, WO2003/041711, WO2003/051368, WO2003/051873, WO2004/026866, WO2004/041791, WO2004/041807, WO2004/041816, WO2009/003993, WO2009/003997, WO2009/124956, WO2010/060470, WO2010/060471, WO2010/060472, WO2010/063662, WO2010/063663, WO2010/072722, WO2010/122151, and WO2008/150364. A particular pyrrolidine derived compound is disclosed in Langmead et. al, Brit. J. Pharmacol. 2004, 141, 340-346 as being highly orexin-1 selective. WO2003/002561 discloses certain N-aroyl cyclic amine derivatives, encompassing benzimidazol-2-yl-methyl substituted pyrrolidine derivatives, as orexin receptor antagonists. Despite the great number of prior art compounds and their high structural variability, all compounds share a common structural feature, i.e. in position 2 of the saturated cyclic amide a linker group such as at least a methylene group (or longer groups such as —CH$_2$—NH—CO—, —CH$_2$—NH—, —CH$_2$—O—, —CH$_2$—S—, etc.) link the cyclic amide to the respective aromatic ring system substituent. Despite the substantial conformational changes that may be expected from the removal of a linker between two rigid structural elements, the compound of the present crystalline salt form, that has a benzimidazole ring directly attached to a pyrrolidine amide in position 2, is a dual antagonist of the orexin 1 receptor and of the orexin 2 receptor and, thus, is of potential use in the treatment of disorders relating to orexinergic dysfunctions, comprising especially sleep disorders, anxiety disorders, addiction disorders, cognitive dysfunctions, mood disorders, or appetite disorders; and especially in the treatment of sleep disorders, anxiety disorders, and addiction disorders.

It has now been found that a crystalline hydrochloride salt form of COMPOUND may under certain conditions be found. Said crystalline salt form of COMPOUND is novel and may have advantageous properties in view of the potential use of COMPOUND as active pharmaceutical ingredient. Such properties may include better flow properties; less hygroscopicity; better reproducibility in manufacturing (for example better filtration parameters, better reproducibility of formation, and/or better sedimentation); and/or defined morphology. Further, such properties may include improved pharmacological and/or pharmacokinetic properties (e.g. higher bioavailability) when compared to the COMPOUND in form of the free base.

Figure 1:
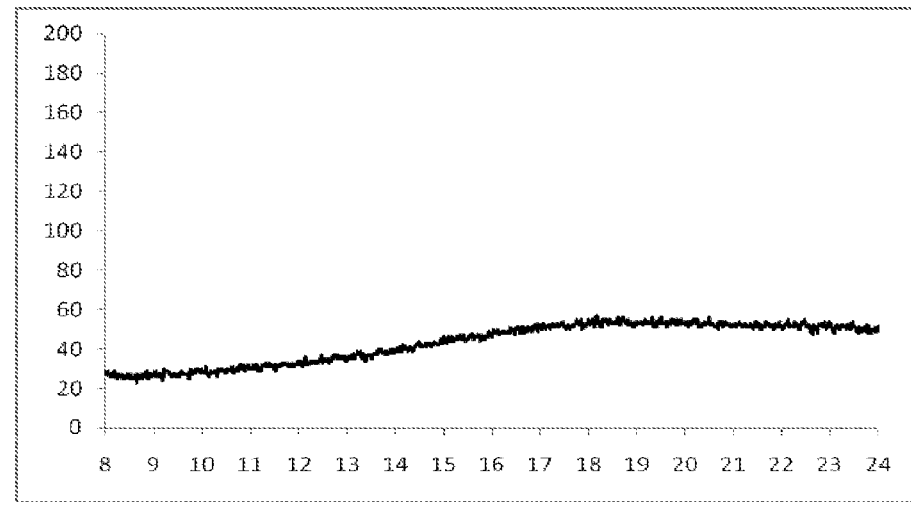
FIG. 1 shows the X-ray powder diffraction diagram of COMPOUND in form of the amorphous free base as obtained from Reference Example 1. The X-ray diffraction diagram measured with method 1 shows amorphous material.
Figure 2:
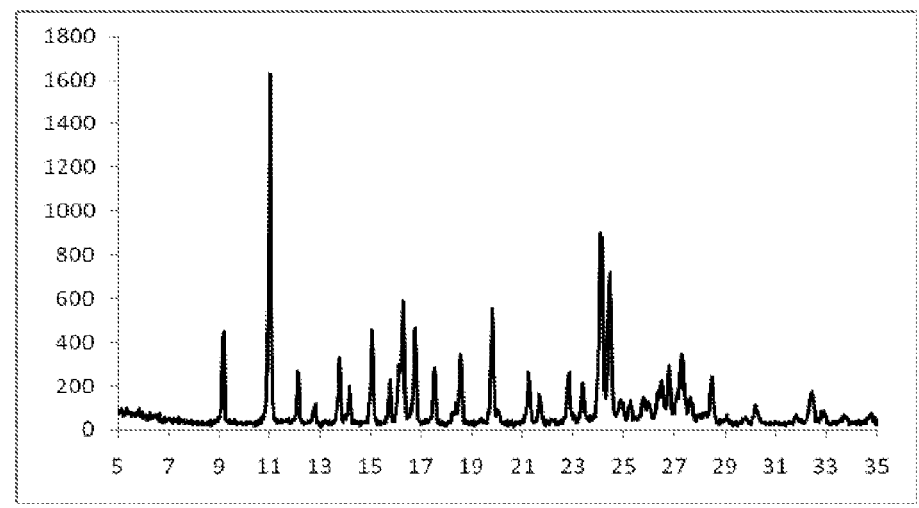
FIG. 2 shows the X-ray powder diffraction diagram of COMPOUND hydrochloride in a crystalline form 1 as obtained from Example 2. The X-ray diffraction diagram measured with method 2 shows peaks having a relative intensity, as compared to the most intense peak in the diagram, of the following percentages (relative peak intensities given in parenthesis) at the indicated angles of refraction 2theta (peaks from the range 3-40° 2theta with relative intensity larger then 10% are reported): 9.2° (28%), 11.0° (100%), 12.1° (17%), 13.8° (20%), 14.2° (12%), 15.1° (28%), 15.8° (14%), 16.3° (36%), 16.8° (28%), 17.5° (18%), 18.6° (21%), 19.8° (34%), 21.2° (16%), 22.8° (16%), 23.4° (13%), 24.1° (55%), 24.5° (44%), 26.5° (14%), 26.8° (18%), 27.3° (21%), 28.5° (15%), and 32.4° (11%). For avoidance of any doubt, the above-listed peaks describe the experimental results of the X-ray powder diffraction shown in FIG. 2. It is understood that, in contrast to the above peak list, only a selection of characteristic peaks is required to fully and unambiguously characterize of the COMPOUND in the crystalline hydrochloride salt form of the present invention.

In the X-ray diffraction diagrams of FIG. 1 and FIG. 2 the angle of refraction 2theta (2θ) is plotted on the horizontal axis and the counts on the vertical axis.

Figure 3:
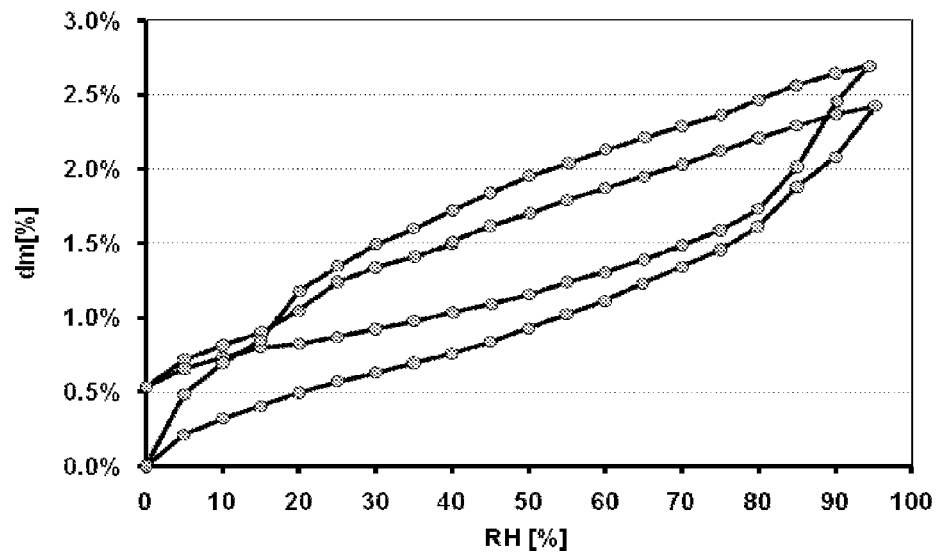

FIG. 3 shows the gravimetric vapour sorption diagram of COMPOUND in amorphous free base form as obtained from Reference Example 1.

Figure 4:
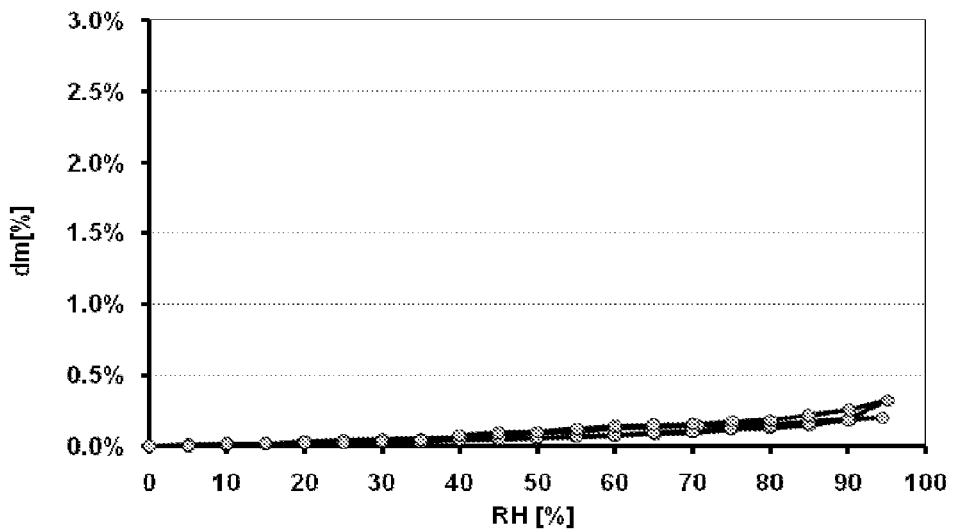

FIG. 4 shows the gravimetric vapour sorption diagram of COMPOUND hydrochloride in a crystalline form 1 as obtained from Example 2.

In the gravimetric vapour sorption diagrams of FIG. 3 and FIG. 4 the relative humidity (% RH) is plotted on the horizontal axis and the mass change (% dm) on the vertical axis.

DETAILED DESCRIPTION OF THE INVENTION

1) The invention relates to a crystalline form of COMPOUND (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone; wherein said COMPOUND is present in form of the hydrochloric acid (hydrochloride) salt; wherein said crystalline salt form is characterized by the presence of peaks in the X-ray powder diffraction diagram at the following angles of refraction 2θ: 11.0°, 24.1° and 24.5°.

It is understood, that the crystalline salt form according to embodiment 1) may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, V C H, 2006), Chapter 8: U. J. Griesser: The Importance of Solvates). Notably such crystalline salt form according to embodiment 1) is an anhydrate, i.e. it does not comprise coordinated water, but may comprise non-coordinated solvent such as isopropanol, ethanol and/or water; especially 0 to about 2 equivalents of any such non-coordinated solvent.

2) Another embodiment relates to a crystalline form of COMPOUND hydrochloride according to embodiment 1), characterized by the presence of peaks in the X-ray powder diffraction diagram at the following angles of refraction 2θ: 9.2°, 11.0°, 13.8°, 15.1°, 16.3°, 16.8°, 19.8°, 24.1°, 24.5°, and 27.3°.

3) Another embodiment relates to a crystalline form of COMPOUND hydrochloride according to embodiments 1) or 2), which essentially shows the X-ray powder diffraction pattern as depicted in FIG. 2.

4) Another embodiment relates to the crystalline form of COMPOUND hydrochloride according to any one of embodiments 1) to 3), which shows an broad endothermic event with peak temperature in the range of about 260° C. to about 290° C. as determined by differential scanning calorimetry (e.g. using the method as described herein).

5) The embodiment further relates to said crystalline hydrochloride salt form according to any one of embodiments 1) to 4), which is obtainable by:
  a) dissolving COMPOUND in about 7 volumes of isopropanol;
  b) heating to about 55° C.;
  c) adding about 4.5% seed crystals of COMPOUND hydrochloride in crystalline form 1 (obtainable for example by using the procedure of example 1 below);
  d) adding about 3.5 volumes of isopropanol;
  e) adding about 0.6 volumes of 5-6 normal HCl in isopropanol;
  f) cooling the suspension to about 20° C. and filtration;
  g) washing the cake with about 3.6 volumes of isopropanol and drying the product at about 60° C. and reduced pressure of about 10 mbar.

The embodiment further relates to the above process for obtaining the crystalline hydrochloride salt form according to any one of embodiments 1) to 4).

For avoidance of any doubt, whenever one of the above embodiments refers to "peaks in the X-ray powder diffraction diagram at the following angles of refraction 2θ", said X-ray powder diffraction diagram is obtained by using using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Where the plural form is used for compounds, solid, pharmaceutical compositions, diseases and the like, this is intended to mean also a single compound, solid, or the like.

The term "enantiomerically enriched" is understood in the context of the present invention to mean especially that at least 90, preferably at least 95, and most preferably at least 99 percent by weight of the COMPOUND are present in form of one enantiomer of the COMPOUND. It is understood that COMPOUND is present in enantiomerically enriched absolute (S)-configuration.

The term "essentially pure" is understood in the context of the present invention to mean especially that at least 90, preferably at least 95, and most preferably at least 99 percent by weight of the crystals of a COMPOUND are present in a crystalline form according to the present invention, especially in a single crystalline form of the present invention.

When defining the presence of peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 2, the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C., notably to an interval extending from Y minus 3° C. to Y plus 3° C. Room temperature means a temperature of about 25° C. When in the current application the term n equivalent(s) is used wherein n is a number, it is meant and within the scope of the current application that n is referring to about the number n, preferably n is referring to the exact number n.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. Likewise, the expression v/v refers to a ratio by volume of the two components considered. The expression "vol" signifies volumes (in L, e.g. of solvent) per weight (in kg, e.g. of reactant). For example 7 vol signifies 7 liters (of solvent) per kg (of reactant).

The crystalline forms, especially the essentially pure crystalline forms, of COMPOUND hydrochloride according to any one of embodiments 1) to 5) can be used as medicaments, e.g. in the form of pharmaceutical compositions for enteral or parenteral administration.

6) Another embodiment thus relates to a crystalline form of COMPOUND (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride according to any one of embodiments 1) to 5) for use as a medicament.

The crystalline solid, especially the essentially pure crystalline solid, of COMPOUND hydrochloride according to any one of embodiments 1) to 5) may be used as single component or as mixtures with other crystalline forms or the amorphous form of COMPOUND.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

7) A further embodiment of the invention relates to pharmaceutical compositions comprising a crystalline form of COMPOUND (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride according to any one of embodiments 1) to 5), and a pharmaceutically acceptable carrier material. Typical carrier materials are for example alpha lactose monohydrate, beta lactose, mannitol, starch, microcrystalline cellulose, hydroxypropylmethylcellulose, sodium carboxymethylcellulose, sodium starch glycolate, croscarmellose sodium, magnesium stearate, compritol, aerosil, talcum, sodium dodecyl sulfate, ascorbic acid, sodium bicarbonate, or calcium hydrogen phosphate.

Such pharmaceutical compositions according to embodiment 7) are especially useful for the prevention or treatment of diseases or disorders related to the orexin system, such as especially sleep disorders, anxiety disorders, addiction disorders, cognitive dysfunctions, mood disorders, or appetite disorders.

8) A further embodiment of the invention relates to a pharmaceutical composition according to embodiment 7), wherein said pharmaceutical composition is in form of a tablet.

9) A further embodiment of the invention relates to a pharmaceutical composition according to embodiment 7), wherein said pharmaceutical composition is in form of a capsule.

10) A further embodiment of the invention relates to a crystalline form of COMPOUND (S)-(2-(6-chloro-7-methyl-1H-benzo[d]imidazol-2-yl)-2-methyl pyrrolidin-1-yl)(5-methoxy-2-(2H-1,2,3-triazol-2-yl)phenyl)methanone hydrochloride according to any one of embodiments 1) to 5), for use in the prevention or treatment of diseases or disorders related to the orexin system, notably mental health diseases or disorders relating to orexinergic dysfunctions.

11) A further embodiment of the invention relates to a crystalline form of COMPOUND (S)-(2-(6-chloro-7-methyl-1H-benzo[d]imidazol-2-yl)-2-methyl pyrrolidin-1-yl)(5-methoxy-2-(2H-1,2,3-triazol-2-yl)phenyl)methanone hydrochloride according to any one of embodiments 1) to 5), for use in the preparation of a medicament for the prevention or treatment of diseases or disorders related to the orexin system, notably mental health diseases or disorders relating to orexinergic dysfunctions.

12) A further embodiment of the invention relates to pharmaceutical compositions according to any one of embodiments 7) to 9), for the prevention or treatment of diseases or disorders related to the orexin system, notably mental health diseases or disorders relating to orexinergic dysfunctions.

13) A further embodiment of the invention relates to any one of embodiments 7) to 9), wherein said diseases or disorders related to the orexin system are mental health diseases or disorders relating to orexinergic dysfunctions selected from the group consisting of sleep disorders, anxiety disorders, addiction disorders, cognitive dysfunctions, mood disorders, and appetite disorders (especially sleep disorders, anxiety disorders, and addiction disorders).

14) A further embodiment of the invention relates to any one of embodiments 7) to 9), wherein said diseases or disorders related to the orexin system are mental health diseases or disorders relating to orexinergic dysfunctions selected from the group consisting of sleep disorders selected from the group consisting of dyssomnias, parasomnias, sleep disorders associated with a general medical condition and substance-induced sleep disorders; anxiety disorders; and addiction disorders.

Such disorders relating to orexinergic dysfunctions are diseases or disorders where an antagonist of a human orexin receptor is required, notably mental health disorders relating to orexinergic dysfunctions. The above mentioned disorders may in particular be defined as comprising sleep disorders, anxiety disorders, addiction disorders, cognitive dysfunctions, mood disorders, or appetite disorders. In one sub-embodiment, the above mentioned disorders comprise especially anxiety disorders, addiction disorders and mood disorders, notably anxiety disorders and addiction disorders. In another sub-embodiment, the above mentioned disorders comprise especially sleep disorders.

In addition, further disorders relating to orexinergic dysfunctions are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; and treating or controlling agitation, in isolation or co-morbid with another medical condition.

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, posttraumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], cannabis, ethanol, mescaline, nicotine, and the like}, which substances/drugs may be consumed alone or in combination; or other rewarding stimuli {of either natural origin (such as food, sweet, fat, or sex, and the like), or synthetic origin

[such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleepwalking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

The present invention also relates to a method for the prevention or treatment of a disease or disorder mentioned herein, comprising administering to a subject a pharmaceutically active amount of a crystalline form of COMPOUND (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride according to any one of embodiments 1) to 5).

The present invention also relates to a process for the preparation of COMPOUND in enantiomerically enriched form, and to processes for the preparation and characterization of crystalline form of COMPOUND (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride according to any one of embodiments 1) to 5). Said processes are described in embodiment 5) as well as in the procedures of the experimental part below.

EXPERIMENTAL PROCEDURES

Abbreviations (as Used Hereinbefore or Hereinafter):
Ac Acetyl (such as in OAc=acetate, AcOH=acetic acid)
AcOH Acetic acid
anh. Anhydrous
aq. aqueous
atm Atmosphere
tBME tert-Butylmethylether
Boc tert-Butoxycarbonyl
$Boc_2O$ di-tert-Butyl dicarbonate
BSA Bovine serum albumine
Bu Butyl such as in tBu=tert-butyl=tertiary butyl
CC Column Chromatography on silica gel
CHO Chinese Hamster Ovary
conc. Concentrated
DCE 1,2-Dichloroethane
DCM Dichloromethane
DEA Diethylamine
DIPEA Diisopropylethylamine
DMF N,N-Dimethylformamide
DMSO Dimethyl sulfoxide
EDC
ELSD Evaporative Light-Scattering Detection
eq Equivalent(s)
ES Electron spray
Et Ethyl
$Et_2O$ Diethyl ether
EtOAc Ethyl acetate
EtOH Ethanol
Ex. Example
FC Flash Chromatography on silica gel
FCS Foatal calf serum
Fig Figure
FLIPR Fluorescent imaging plate reader
h Hour(s)
HATU 1-[Bis(dimethylamino)methylene]-1H-1,2,3-triazolo[4,5-b]pyridinium 3-oxid hexafluorophosphate
HBSS Hank's balanced salt solution
HBTU N,N,N'N'-Tetramethyl-O-(1H-benzotriazol-1-yl)uronium hexafluorophosphate
HEPES 4-(2-Hydroxyethyl)-piperazine-1-ethanesulfonic acid
$^1$H-NMR Nuclear magnetic resonance of the proton
HPLC High performance liquid chromatography
LC-MS Liquid chromatography-Mass Spectroscopy
Lit. Literature
M Exact mass (as used for LC-MS)
Me Methyl
MeCN Acetonitrile
MeOH Methanol
MeI Methyl iodide
MHz Megahertz
μl microliter
min Minute(s)
MS Mass spectroscopy
N Normality
$Pd(OAc)_2$ Palladium diacetate
$Pd(PPh_3)_4$ Tetrakis(triphenylphosphine)palladium(0)
$PL-HCO_3$ Polymer supported hydrogen carbonate
Ph Phenyl
$PPh_3$ Triphenylphosphine
prep. Preparative
RT Room temperature
sat. Saturated
TBTU O-(Benzotriazol-1-yl)-N,N,N',N'-tetramethyluronium tetrafluoroborate
TEA Triethylamine
TFA trifluoroacetic acid
Tf Trifluoromethansulfonyl
THF Tetrahydrofuran
$t_R$ Retention time
UV Ultra violet
I-Chemistry All temperatures are stated in ° C. The commercially available starting materials were used as received without further purification. Compounds are purified by flash column chromatography over silica gel (FC), column chromatography over silica gel (CC), or by preparative HPLC. Compounds described in the invention are characterized by LC-MS (retention time $t_R$ is given in min.; molecular weight obtained from the mass spectrum is given in g/mol, using the conditions listed below). If the mass is not detectable the compounds are also characterized by $^1$H-NMR (400 MHz: Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz).

Preparative HPLC for Purification of Compounds (Conditions C)

Column: Waters XBridge (10 μm, 75×30 mm). Conditions: MeCN [eluent A]; water+0.5% $NH_4OH$ (25% aq.) [eluent B]; Gradient: 90% B→5% B over 6.5 min. (flow: 75 ml/min.). Detection: UV+ELSD.

Preparative HPLC for Purification of Compounds (Conditions D)

Column: Waters Atlantis T3 OBD (10 μm, 75×30 mm). Conditions: MeCN [eluent A]; water+0.5% HCOOH [eluent B]; Gradient: 90% B→5% B over 6.4 min. (flow: 75 ml/min.). Detection: UV+ELSD.

LC-MS with Acidic Conditions

Apparatus: Agilent 1100 series with mass spectroscopy detection (MS: Finnigan single quadrupole). Column: Agilent Zorbax SB-Aq, (3.5 um, 4.6×50 mm). Conditions: MeCN [eluent A]; water+0.04% TFA [eluent B]. Gradient: 95% B→5% B over 1.5 min. (flow: 4.5 ml/min.). Detection: UV+MS.

X-ray Powder Diffraction Analysis

X-ray powder diffraction patterns were collected on a Bruker D8 Advance X-ray diffractometer equipped with a Lynxeye detector operated with $CuK_\alpha$-radiation in reflection mode (coupled two Theta/Theta). Typically, the X-ray tube was run at of 40 kV/40 mA. A step size of 0.02° (2θ) and a step time of 76.8 sec over a scanning range of 3-50° in 2θ were applied. The divergence slit was set to fixed 0.3. Powders were slightly pressed into a silicon single crystal sample holder with depth of 0.5 mm and samples were rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Gravimetric Vapour Sorption (GVS) Analysis

Measurements were performed simultaneously for the amorphous COMPOUND and COMPOUND hydrochloride crystalline Form 1 on a multi sample instrument SPS-100n (Projekt Messtechnik, Ulm, Germany) operated in stepping mode at 25° C. The sample was allowed to equilibrate at 40% RH before starting a pre-defined humidity program (40-0-95-0-95-40% RH, steps of 5% ΔRH and with a maximal equilibration time of 24 hours per step were applied. About 20 to 30 mg of each sample was used. The hygroscopic classification is done according to the European Pharmacopeia Technical Guide (1999, page 86), e.g., slightly hygroscopic: increase in mass is less than 2% and equal to or greater than 0.2% mass/mass; hygroscopic: increase in mass is less than 15% and equal to or greater than 2% mass/mass. The mass change between 40% relative humidity and 80% relative humidity in the first adsorption scan is considered.

Differential Scanning Calorimetry

DSC data were collected on a Mettler Toledo STARe System (DSC822e module, measuring cell with ceramic sensor and STAR software version 9.20) equipped with a 34 position auto-sampler. The instrument was calibrated for energy and temperature using certified indium. Typically 1-5 mg of each sample, in a automatically pierced aluminium pan, was heated at 10° C. min$^{-1}$, unless stated otherwise, from −20° C. to 280° C. A nitrogen purge at 20 ml min$^{-1}$ was maintained over the sample.

Reference Example 1

1) Synthesis of 5-methoxy-2-(2H-1,2,3-triazol-2-yl)benzoic acid

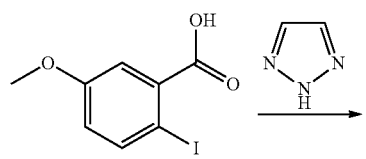

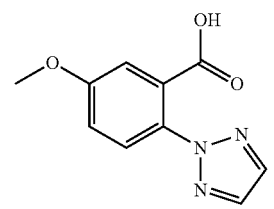

2-Iodo-5-methoxy benzoic acid (15.0 g; 53.9 mmol) is dissolved in anhydrous DMF (45 ml) followed by the addition of 1H-1,2,3-triazole (7.452 g; 108 mmol) and cesium carbonate (35.155 g; 108 mmol). By the addition of cesium carbonate the temperature of the reaction mixture increases to 40° C. and gas evolved from the reaction mixture. Copper(I)iodide (514 mg; 2.7 mmol) is added. This triggers a strongly exothermic reaction and the temperature of the reaction mixture reaches 70° C. within a few seconds. Stirring is continued for 30 minutes. Then the DMF is evaporated under reduced pressure followed by the addition of water (170 ml) and EtOAc (90 ml). The mixture is vigorously stirred and by the addition of citric acid monohydrate the pH is adjusted to 3-4. The precipitate is filtered off and washed with water and EtOAc and discarded. The filtrate is poured into a separation funnel and the phases are separated. The water phase is extracted again with EtOAc. The combined organic layers are dried over MgSO$_4$, filtered and the solvent is evaporated to give 7.1 g of 5-methoxy-2-(2H-1,2,3-triazol-2-yl)benzoic acid as a white powder of 94% purity (6% impurity is the regioisomerically N1-linked triazolo-derivative); $t_R$ [min]=0.60; [M+H]$^+$=220.21

2) Synthesis of (S)-1-(tert-butoxycarbonyl)-2-methylpyrrolidine-2-carboxylic acid

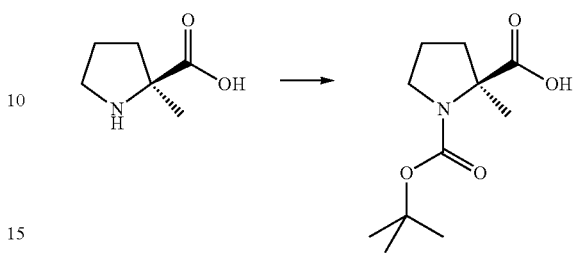

2-Methyl-L-proline hydrochloride (99.7 g; 602 mmol) is dissolved in a 1/1-mixture of MeCN and water (800 ml) and triethylamine (254 ml; 1810 mmol) is added. The temperature of the reaction mixture slightly rises. The reaction mixture is cooled to 10° C. to 15° C. followed by careful addition of a solution of Boc$_2$O (145 g; 662 mmol) in MeCN (200 ml) over 10 minutes. Stirring at RT is continued for 2 hours. The MeCN is evaporated under reduced pressure and aq. NaOH solution (2M; 250 ml) is added to the residual aq. part of the reaction mixture. The water layer is washed with Et$_2$O (2×300 ml) then cooled to 0° C. followed by slow and careful addition of aq. HCl (25%) to adjust the pH to 2. During this procedure a suspension forms. The precipitate is filtered off and dried at HV to give 110.9 g of the title compound as a beige powder; $t_R$ [min]=0.68; [M+H]$^+$=230.14

3) Synthesis of (S)-tert-butyl 2-((2-amino-4-chloro-3-methylphenyl)carbamoyl)-2-methylpyrrolidine-1-carboxylate

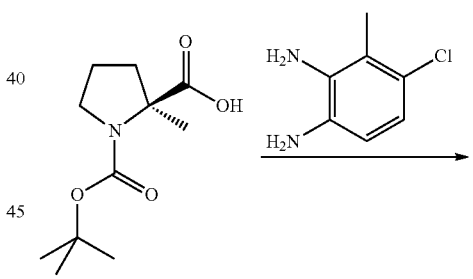

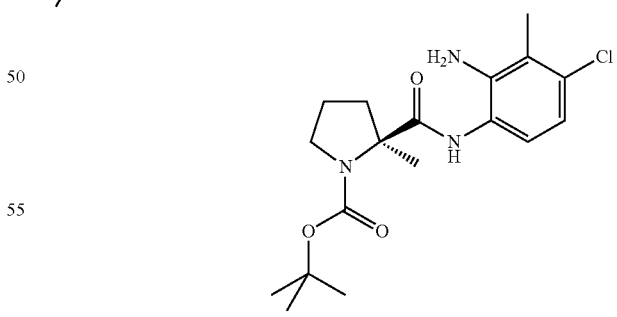

(S)-1-(tert-butoxycarbonyl)-2-methylpyrrolidine-2-carboxylic acid (60 g; 262 mmol) and HATU (100 g; 264 mmol) is suspended in DCM (600 ml) followed by the addition of DIPEA (84.6 g; 654 mmol) and 6-chloro-2,3-diaminotoluene (41 g; 262 mmol). The reaction mixture is stirred at rt for 14 hours then concentrated under reduced pressure and to the residue is added water followed by the extraction of the product with EtOAc (3×). The combined organic layers are washed with brine, dried over MgSO₄, filtered and the solvent is evaporated under reduced pressure to give 185 g of the title compound as a dark brownish oil, which is used in the next step without further purification; $t_R$ [min]=0.89; [M+H]⁺=368.01

4) Synthesis of (S)-tert-butyl 2-(5-chloro-4-methyl-1H-benzo[d]imidazol-2-yl)-2-methylpyrrolidine-1-carboxylate

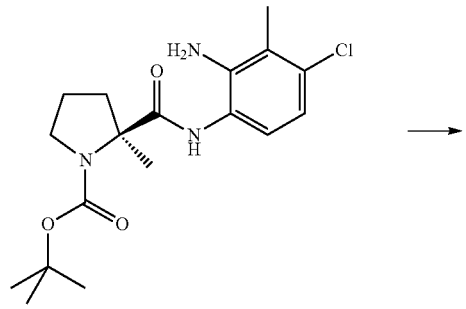

(S)-tert-butyl 2-((2-amino-4-chloro-3-methylphenyl)carbamoyl)-2-methylpyrrolidine-1-carboxylate (185 g; 427 mmol) are dissolved in AcOH (100%; 611 ml), heated to 100° C. and stirring continued for 90 minutes. The AcOH is evaporated under reduced pressure and the residue is dissolved in DCM followed by careful addition of saturated sodium bicarbonate solution. The phases are separated, the aq. phase is extracted once more with DCM, the combined aq. phases are dried over MgSO₄, filtered and the solvent is evaporated under reduced pressure to give 142.92 g of the title compound as a dark brown oil which is used in the next step without further purification; $t_R$ [min]=0.69; [M+H]⁺=350.04

5) Synthesis of (S)-5-chloro-4-methyl-2-(2-methylpyrrolidin-2-yl)-1H-benzo[d]imidazole hydrochloride

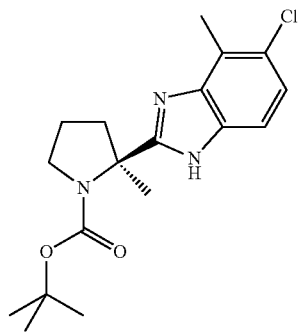

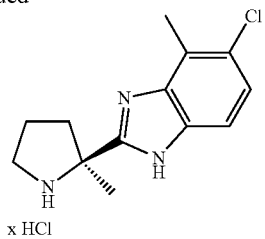

(S)-tert-butyl 2-(5-chloro-4-methyl-1H-benzo[d]imidazol-2-yl)-2-methylpyrrolidine-1-carboxylate (355.53 g; 1.02 mol) are dissolved in dioxane (750 ml) followed by careful addition of HCl solution in dioxane (4M; 750 ml; 3.05 mol). The reaction mixture is stirred for 3 hours followed by the addition of Et₂O (800 ml) which triggered precipitation of the product. The solid is filtered off and dried at high vacuum to give 298.84 g of the title compound as a redish powder; $t_R$ [min]=0.59; [M+H]⁺=250.23

6) Synthesis of [(S)-2-(5-chloro-4-methyl-1H-benzoimidazol-2-yl)-2-methyl-pyrrolidin-1-yl]-(5-methoxy-2-[1,2,3]triazol-2-yl-phenyl)-methanone

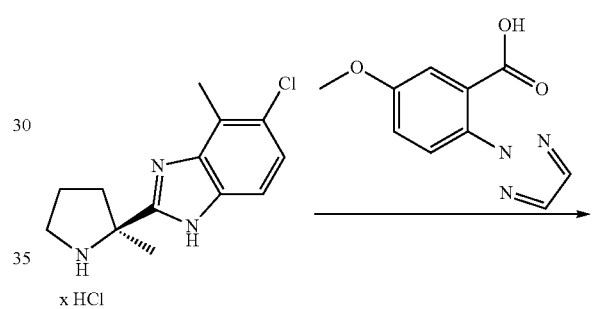

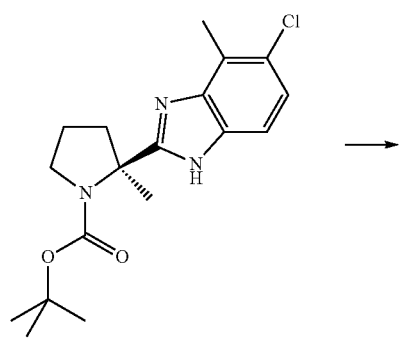

(S)-5-chloro-4-methyl-2-(2-methylpyrrolidin-2-yl)-1H-benzo[d]imidazole hydrochloride (62.8 g; 121 mmol) is dissolved in DCM (750 ml) followed by the addition of 5-methoxy-2-(2H-1,2,3-triazol-2-yl)benzoic acid (62.8 g; 121 mmol) and DIPEA (103 ml; 603 mmol). Stirring is continued for 10 minutes followed by the addition of HATU (47 g; 124 mmol). The reaction mixture is stirred for 16 hours at RT. The solvents are evaporated under reduced pressure and the residue is dissolved in EtOAc (1000 ml) and washed with water (3×750 ml). The organic phase is dried over MgSO₄, filtered and the solvent is evaporated under reduced pressure. The residue is purified by CC with EtOAc/hexane=2/1 to give 36.68 g of the title compound as an amorphous white powder. $t_R$ [min]=0.73; [M+H]⁺=450.96

TABLE 1

Characterisation data for COMPOUND as free base in amorphous form

| Technique | Data Summary | Remarks |
| --- | --- | --- |
| XRPD | Amorphous | see FIG. 1 |
| Elemental analysis | Consistent. | |
| Hygroscopicity | Slightly hygroscopic (mass change of about 0.7%), Hysteresis and sorption of up to 2.7% moisture mass/mass. Variability in sorption behavior first to second cycle | see FIG. 3 |

II. Preparation of Crystalline Forms of COMPOUND

Example 1

Preparation of Seeding Material of COMPOUND Hydrochloride in Crystalline Form 1

10 mg COMPOUND is mixed with 0.2 mL 0.1M aq. HCl and 0.8 mL EtOH. The solvent is fully evaporated and 0.05 mL isopropanol is added. Alternatively 0.05 mL methylisobutylketone can be added. The sample is stored closed at room temperature for 4 days and crystalline material of COMPOUND hydrochloride in crystalline Form 1 is obtained. This material can be used as seeding material for further crystallization of COMPOUND hydrochloride in crystalline Form 1.

Example 2

Preparation and Characterization of COMPOUND Hydrochloride in Crystalline Form 1

5 g COMPOUND is mixed with 0.9 mL 1M aq. HCl and 20 mL EtOH. The solvent is evaporated and 25 mL isopropanol is added. Seeds of COMPOUND hydrochloride are added and the sample is allowed to stand at room temperature. After about 2 days the suspension is filtered and the solid residue is dried at reduced pressure (2 mbar for 1 hour) and allowed to equilibrate open for 2 hours at 24° C./46% relative humidity. The obtained solid is COMPOUND hydrochloride in crystalline Form 1

TABLE 2

Characterisation data for COMPOUND hydrochloride in crystalline form 1

| Technique | Data Summary | Remarks |
| --- | --- | --- |
| XRPD | Crystalline | see FIG. 2 |
| DSC | Broad endothermic event with peak temperature in the range of about 260° C. to about 290° C. | |
| Elemental analysis | Consistent | |
| Hygroscopicity | Non hygroscopic (mass change smaller then 0.1%). Reproducible, cycle independent sorption/desorption behavior. | See FIG. 4 |

III. Biological Assays

To further characterize the biological activity of COMPOUND, antagonistic activities on both orexin receptors have been measured using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH: water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at RT for 30 min before measurement.

Within the Fluorescent Imaging Plate Reader (FLIPR Tetra, Molecular Devices), antagonists are added to the plate in a volume of 10 µl/well, incubated for 120 min and finally 10 µl/well of agonist is added. Fluorescence is measured for each well at 1 second intervals, and the height of each fluorescence peak is compared to the height of the fluorescence peak induced by an approximate $EC_{70}$ (for example 5 nM) of orexin-A with vehicle in place of antagonist. The $IC_{50}$ value (the concentration of compound needed to inhibit 50% of the agonistic response) is determined and may be normalized using the obtained $IC_{50}$ value of a on-plate reference compound. Optimized conditions are achieved by adjustment of pipetting speed and cell splitting regime. The calculated $IC_{50}$ values may fluctuate depending on the daily cellular assay performance. Fluctuations of this kind are known to those skilled in the art. Average $IC_{50}$ values from several measurements are given as mean values.

COMPOUND has been measured on the orexin-1 receptor with an $IC_{50}$ value of 2 nM.

COMPOUND has been measured on the orexin-2 receptor with an $IC_{50}$ value of 3 nM.

Measurement of Brain and Systemic Concentration After Oral Administration:

In order to assess brain penetration, the concentration of the compound is measured in plasma ([P]), and brain ([B]), sampled 3 h (or at different time points) following oral administration (e.g. 100 mg/kg) to male wistar rats. The compound is formulated e.g. in 100% PEG 400. Samples are collected in the same animal at the same time point (+/−5 min). Blood is sampled from the vena cava caudalis into containers with EDTA as anticoagulant and centrifuged to yield plasma. Brain is sampled after cardiac perfusion of 10 mL NaCl 0.9% and homogenized into one volume of cold phosphate buffer (pH 7.4). All samples are extracted with MeOH and analyzed by LC-MS/MS. Concentrations are determined with the help of calibration curves.

Results obtained for COMPOUND:

3 h after oral administration (100 mg/kg), n=3): [P]=1280 ng/ml; [B]=1808 ng/g.

Sedative Effects: EEG, EMG and Behavioural Indices of Alertness Recorded by Radiotelemetry In Vivo in Wistar Rats.

Electroencephalography (EEG) and Electromyography (EMG) signals were measured by telemetry using TL11M2-F20-EET miniature radiotelemetric implants (Data Science Int.) with two pairs of differential leads.

Surgical implantation was performed under general anesthesia with Ketamin/Xylazin, for cranial placement of one differential pair of EEG electrodes and one pair of EMG leads inserted in either side of the muscles of the neck. After surgery, rats recovered in a thermoregulated chamber and received analgesic treatment with subcutaneous buprenorphine twice a day for 2 d. They were then housed individually and allowed to recover for a minimum of 2 weeks. Thereafter, rats—in their home cage—were placed in a ventilated sound-attenuating box, on a 12-h light/12-h dark cycle, for acclimatization before continuous EEG/EMG recordings started. The telemetric technology that we used in this study allows accurate and stress-free acquisition of biosignals in rats placed in their familiar home cage environment, with no recording leads restricting their movements. Variables analyzed included four different stages of vigilance and sleep, spontaneous activity in the home cage and body temperature. Sleep and wake stages were evaluated using a rodent scoring software (Somnologica Science) directly processing electrical biosignals on 10 s contiguous epochs. The scoring is based on frequency estimation for EEG and amplitude discrimination for EMG and locomotor activity. Using these measurements, the software determines the probability that all components within each epoch best represent active waking (AW), quiet waking (QW), non-REM-sleep (NREM) or REM-sleep (REM). The percentage of total time spent in AW, QW, NREM- and REM-sleep was calculated per 12 h light or dark period. The latency to the onset of the first significant NREM- and REM-sleep episodes and the frequency and duration of those episodes were also calculated. AW, QW, NREM- and REM-sleep, home cage activity and body temperature were measured at baseline for at least one total circadian cycle (12 h-night, 12 h-day) before a test compound was administered. If baseline measurements indicated that animals were stable, test compound or vehicle was given in the evening by oral gavage at the end of the baseline 12-h day period, immediately before the nocturnal rise in orexin and activity in rats. All variables were subsequently recorded for 12 h following administration of the orexin receptor antagonist.

COMPOUND has been tested in this assay (oral dosage: 30 mg/kg po; effects analyzed over 6 hours): Results are: −24% on active wake, −31% on home cage activity, +27% on NREM sleep, +53% on REM sleep; when compared to vehicle controls.

The invention claimed is:

1. A method of treatment of a sleep disorder, an anxiety disorder, or an addiction disorder, a cognitive dysfunction, a mood disorder, or an appetite disorder; comprising administering to a patient an effective amount of the compound (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride in crystalline form; wherein said crystalline form comprises peaks in the X-ray powder diffraction diagram at the following angles of refraction 2θ: 11.0°, 24.1° and 24.5°, wherein said X-ray powder diffraction diagram is obtained by using combined Cu Kα1 and Kα2 radiation, without Kα2 stripping; and the accuracy of the 2θ values is in the range of 2θ+/−0.2°.

2. The method of claim 1, wherein said crystalline form comprises peaks in the X-ray powder diffraction diagram at the following angles of refraction 2θ: 9.2°, 11.0°, 13.8°, 15.1°, 16.3°, 16.8°, 19.8°, 24.1°, 24.5°, and 27.3°, wherein said X-ray powder diffraction diagram is obtained by using combined Cu Kα1 and Kα2 radiation, without Kα2 stripping; and the accuracy of the 2θ values is in the range of 2θ+/−0.2°.

3. The method of claim 1, wherein said crystalline form essentially shows the X-ray powder diffraction pattern as depicted in FIG. 2.

4. The method of claim 2, wherein the sleep disorder is a dyssomnia, a parasomnia, a sleep disorders associated with a general medical condition, or a substance-induced sleep disorder.

5. The method of claim 4, wherein the anxiety disorder is a post-traumatic stress disorder, an obsessive compulsive disorder, a panic attack, a phobic anxiety, or an avoidance.

6. A method of treatment of a sleep disorder; comprising administering to a patient an effective amount of the compound (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride in crystalline form; wherein said crystalline form comprises peaks in the X-ray powder diffraction diagram at the following angles of refraction 2θ: 11.0°, 24.1° and 24.5°, wherein said X-ray powder diffraction diagram is obtained by using combined Cu Kα1 and Kα2 radiation, without Kα2 stripping; and the accuracy of the 2θ values is in the range of 2θ+/−0.2°.

7. The method of claim 6, wherein said crystalline form comprises peaks in the X-ray powder diffraction diagram at the following angles of refraction 2θ: 9.2°, 11.0°, 13.8°, 15.1°, 16.3°, 16.8°, 19.8°, 24.1°, 24.5°, and 27.3°, wherein said X-ray powder diffraction diagram is obtained by using combined Cu Kα1 and Kα2 radiation, without Kα2 stripping; and the accuracy of the 2θ values is in the range of 2θ+/−0.2°.

8. The method of claim 7, wherein the sleep disorder is a dyssomnia, a parasomnia, a sleep disorder associated with a general medical condition, or a substance-induced sleep disorder.

9. The method of claim 7, wherein the sleep disorder is an insomnia, a sleep-related dystonia; a restless leg syndrome; a sleep apnea; a jet-lag syndrome; a shift work sleep disorder, a delayed or advanced sleep phase syndrome, or an insomnia related to psychiatric disorders.

10. The method of claim 7, wherein the sleep disorder is an insomnia.

11. A method of treatment of an anxiety disorder; comprising administering to a patient an effective amount of the compound (S)-(2-(6-chloro-7-methyl-1H-benzo[d]imidazol-2-yl)-2-methylpyrrolidin-1-yl)(5-methoxy-2-(2H-1,2,3-triazol-2-yl)phenyl)methanone hydrochloride in crystalline form; wherein said crystalline form comprises peaks in the X-ray powder diffraction diagram at the following angles of refraction 2θ: 11.0°, 24.1° and 24.5°, wherein said X-ray powder diffraction diagram is obtained by using combined Cu Kα1 and Kα2 radiation, without Kα2 stripping; and the accuracy of the 2θ values is in the range of 2θ+/−0.2°.

12. The method of claim 11, wherein said crystalline form comprises peaks in the X-ray powder diffraction diagram at the following angles of refraction 2θ: 9.2°, 11.0°, 13.8°, 15.1°, 16.3°, 16.8°, 19.8°, 24.1°, 24.5°, and 27.3°, wherein said X-ray powder diffraction diagram is obtained by using combined Cu Kα1 and Kα2 radiation, without Kα2 stripping; and the accuracy of the 2θ values is in the range of 2θ+/−0.2°.

13. The method of claim 12, wherein the anxiety disorder is a post-traumatic stress disorder, an obsessive compulsive disorder, a panic attack, a phobic anxiety, or an avoidance.

* * * * *